United States Patent
Son (10) Patent No.: US 10,820,886 B2
(45) Date of Patent: Nov. 3, 2020

(54) ULTRASONIC PROBE

(71) Applicant: SAMSUNG MEDISON CO., LTD.

(72) Inventor: Won Kyu Son, Daegu (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 720 days.

(21) Appl. No.: 15/468,869

(22) Filed: Mar. 24, 2017

(65) Prior Publication Data

US 2018/0161004 A1    Jun. 14, 2018

(30) Foreign Application Priority Data

Dec. 14, 2016  (KR) .......................... 10-2016-0170186

(51) Int. Cl.
| | | |
|---|---|---|
| *A61B 8/00* | (2006.01) | |
| *G01N 31/22* | (2006.01) | |
| *A61L 2/26* | (2006.01) | |

(52) U.S. Cl.
CPC .......... *A61B 8/4422* (2013.01); *A61B 8/4411* (2013.01); *A61B 8/4444* (2013.01); *A61B 8/4455* (2013.01); *A61L 2/26* (2013.01); *G01N 31/22* (2013.01); *A61B 8/4405* (2013.01); *A61L 2202/24* (2013.01)

(58) Field of Classification Search
CPC ... A61B 8/4422; A61B 8/4411; A61B 8/4444; A61B 8/4455; A61B 8/4405; A61B 2560/06; A61L 2/26; A61L 2202/24; G01N 31/22
See application file for complete search history.

(56) References Cited

U.S. PATENT DOCUMENTS

| 5,795,632 | A | 8/1998 | Buchalter |
|---|---|---|---|
| 9,218,452 | B2 * | 12/2015 | Varna ..................... G16H 10/60 |
| 2007/0167810 | A1 | 7/2007 | Ito |
| 2008/0139944 | A1 | 6/2008 | Weymer et al. |
| 2009/0266289 | A1 | 10/2009 | Greene et al. |
| 2010/0292575 | A1 | 11/2010 | Sharp |
| 2011/0316696 | A1 | 12/2011 | Yao et al. |
| 2015/0050196 | A1 | 2/2015 | Chan et al. |
| 2015/0245822 | A1 | 9/2015 | Kim et al. |

FOREIGN PATENT DOCUMENTS

| EP | 1165151 | 1/2002 |
|---|---|---|
| JP | 2009-034212 A | 2/2009 |
| KR | 10-1482996 B1 | 1/2015 |
| WO | 2013191060 A1 | 12/2013 |

OTHER PUBLICATIONS

Extended European Search Report dated Dec. 5, 2017 issued in European Patent Application No. 17160511.6.

* cited by examiner

*Primary Examiner* — Joel Lamprecht
(74) *Attorney, Agent, or Firm* — Morgan, Lewis & Bockius LLP

(57) ABSTRACT

Disclosed herein is an ultrasonic probe including an indicator for detecting whether a disinfectant or a cleaner is allowed to be used and thus can prevent from being chemically deformed or damaged by an unallowable disinfectant or an unallowable cleaner.

16 Claims, 6 Drawing Sheets

ULTRASONIC PROBE

CROSS-REFERENCE TO RELATED APPLICATION

This application claims the benefit of Korean Patent Application No. 10-2016-0170186, filed on Dec. 14, 2016 in the Korean Intellectual Property Office, the disclosure of which is incorporated herein by reference.

BACKGROUND

1. Field

Embodiments of the present disclosure relate to an ultrasonic probe for obtaining an ultrasonic image.

2. Description of the Related Art

As an example of a medical apparatus, an ultrasonic imaging apparatus is an apparatus in which an ultrasonic signal is emitted from a surface of an object body toward a target part therein and a tomographic image of soft tissue or an image of a blood flow is obtained without invasiveness using information of a reflected ultrasonic signal (an ultrasonic echo signal).

Since the ultrasonic imaging system is smaller and cheaper than other image diagnostic apparatuses such as an X-ray diagnostic apparatus, an X-ray computerized tomography (CT) scanner, a magnetic resonance image (MRI) apparatus and a nuclear medicine diagnostic apparatus, allows an image to be displayed in real time and also has high safety without radiation exposure, it is widely used in a diagnosis of a heart or abdominal area, an urinary system and obstetrical/gynecological diseases.

Such an ultrasonic imaging system includes a probe for emitting the ultrasonic signal and receiving the reflected ultrasonic signal (the ultrasonic echo signal) and a main body for controlling the ultrasonic signal emitted through the probe or generating a necessary image using the received ultrasonic signal.

SUMMARY

Therefore, it is an aspect of the present disclosure to provide an ultrasonic probe including an indicator for previously checking whether a disinfectant or a cleaner is allowed to be used.

Additional aspects of the disclosure will be set forth in part in the description which follows and, in part, will be obvious from the description, or may be learned by practice of the disclosure.

In accordance with one aspect of the present disclosure, an ultrasonic probe includes a case in which an ultrasonic wave transmitting and receiving device is accommodated; a lens provided at one end of the case; and an indicator attached to an outer surface of the case and including a reacting part configured to react with a certain chemical component.

The indicator may be disposed adjacent to the lens.

The indicator may include a plurality of reacting parts, and the plurality of reacting parts may react with chemical components different from each other, respectively.

The reacting part may include a material of which a color is changed when reacting with a certain chemical component.

The reacting part may include a material of which the color is changed in stages according to a concentration of the certain chemical material or changed into different color according to the concentration of the certain chemical material.

The reacting part may include a material disappeared by reacting with a certain chemical component.

The reacting part may be configured so that a background of a color different from that of the material is exposed when the material is disappeared.

The indicator may be replaceably attached to the case.

The indicator may further include an information provider providing information for checking whether the reacting part reacts.

The information provider may be configured to provide information of a name or a concentration of the certain chemical component with which the reacting part reacts.

The indicator may include a plurality of reacting parts, and each of the plurality of reacting parts may react according to a concentration of the certain chemical component.

In accordance with another aspect of the present disclosure, an ultrasonic probe includes a case in which an ultrasonic wave transmitting and receiving device is accommodated; a lens provided at one end of the case; a cap separably coupled to the case to protect the lens; and an indicator including a reacting part configured to react with a certain chemical component. The cap may include a hole or a mesh provided to allow a disinfectant or a cleaner to pass therethrough.

The indicator may be attached to an outer surface of the cap.

The indicator may be attached to an outer surface of the case adjacent to the lens.

The case may include a groove for checking left and right directions of the lens, and the cap includes a hook coupled to the groove.

The cap may be configured to be spaced apart from the lens at a predetermined distance when being coupled with the case.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Exemplary embodiments described in the specification and configurations illustrated in the drawings are simply the most preferable embodiments of the present disclosure, and thus it should be understood that various modified examples which can replace them are present at the time when the present disclosure is filed.

In the specification, the same reference numerals or symbols provided in each of the drawings denote components or elements that perform substantially the same functions.

Also, the terms used herein are merely to describe a specific embodiment, and do not limit the present disclosure. Further, unless the context clearly indicates otherwise, singular expressions should be interpreted to include plural expressions. It is understood that terms "comprises," "includes" or "has" are intended to indicate the presence of features, numerals, steps, operations, elements and components described in the specification or the presence of combinations of these, and do not preclude the presence of one or more other features, numerals, steps, operations, elements and components, the presence of combinations of these, or additional possibilities.

Also, the terms including ordinal numbers such as "first," "second," etc. can be used to describe various components, but the components are not limited by those terms. The terms are used merely for the purpose of distinguishing one component from another. For example, a first component may be called a second component, and similarly, a second component may be called a first component without departing from the scope of rights of the disclosure. The term "and/or" encompasses combinations of a plurality of items or any one of the plurality of items.

Meanwhile, the terms such as "front end", "rear end", "upper portion", "lower portion", "upper end" and "lower end" used in the following descriptions are defined on the basis of drawings, and a shape and a position of each element should not be limited by the terminology.

Hereinafter, exemplary embodiments of the present disclosure will be described in detail with reference to the attached drawings.

Figure 1:
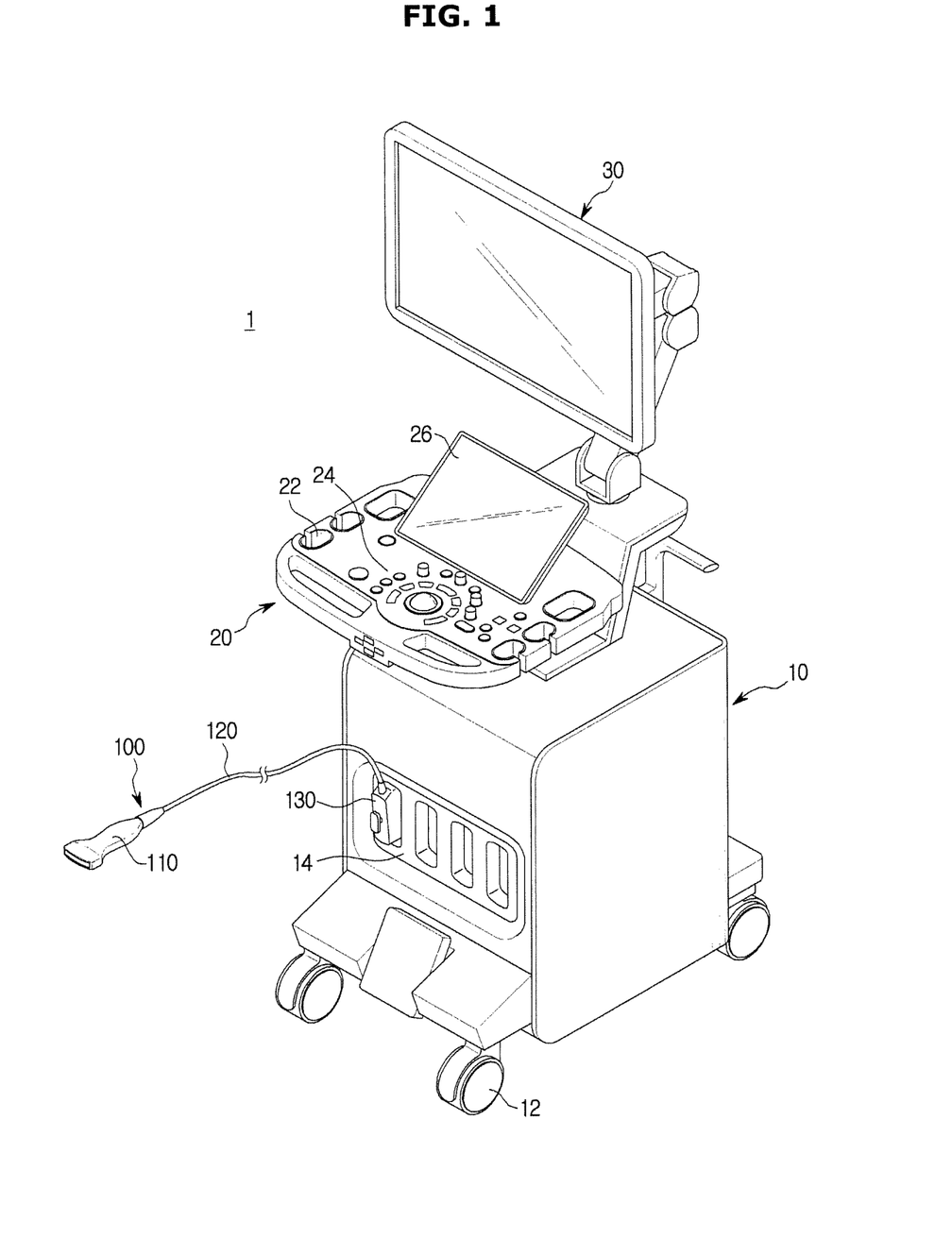
FIG. 1 is a perspective view illustrating a medical apparatus in which an ultrasonic probe according to one embodiment of the present disclosure is allowed to be used.

FIG. 1 is a perspective view illustrating a medical apparatus in which an ultrasonic probe according to one embodiment of the present disclosure is allowed to be used.

Referring to FIG. 1, a medical apparatus 1 according to one embodiment includes a main body 10 and an ultrasonic probe 100 for transmitting an ultrasonic signal to an object to be diagnosed and receiving a signal reflected from the object. The ultrasonic probe 100 may be connected to the main body 10 by a cable.

The ultrasonic probe 100 may be supported at the main body 10 by a holder 22. A user may keep the ultrasonic probe 100 in the holder 22 when not using the medical apparatus 1. FIG. 1 illustrates a state in which the holder 22 for supporting the ultrasonic probe 100 is provided at a control panel 20. However, the holder 22 may be provided at the main body 10 for the user's convenience. Also, the holder 22 may be provided at both of the main body 10 and the control panel 20.

A moving device 12 for moving the medical apparatus 1 may be provided at the main body 10. The moving device 12 may be a plurality of casters provided at a lower surface of the main body 10. The casters may be aligned to allow the main body 10 to be moved in a certain direction, may be provided to be freely movable, thereby being movable in any directions or may be locked to be stopped at a certain position.

The ultrasonic probe 100 includes an ultrasonic wave transmitting and receiving device provided in a case 110. The ultrasonic wave transmitting and receiving device may be configured with a transducer module for emitting an ultrasonic wave to the object, receiving an echo ultrasonic wave reflected from the object and mutually converting an electric signal and the ultrasonic wave. The ultrasonic probe 100 includes a male connector 130 physically coupled with a female connector 14 of the main body 10 to transmit and receive a signal to/from the main body 10 and a cable 120 for connecting the male connector 130 and the transducer module.

Here, the object may be a living body of a human being or an animal, or tissues in the living body thereof such as blood vessels, bones and muscles. However, the object is not limited thereto, as long as an image of an internal structure thereof may be taken by the medical apparatus 1, i.e., an ultrasonic imaging system.

The echo ultrasonic wave is an ultrasonic wave reflected from the object to which the ultrasonic wave is emitted and has a variety of frequency bands or energy intensity for generating various ultrasonic images according to a diagnosis mode.

The transducer module may generate the ultrasonic wave according to AC power applied thereto. Specifically, the transducer module may receive the AC power from an external power supply or an internal electric condenser, e.g., a battery or the like. A vibrator of the transducer module is vibrated according to the applied AC power, and thus the ultrasonic wave may be generated.

One end of the cable 120 is connected to the transducer module and the other end thereof is connected to the male connector 130, and thus the transducer module and the male connector 130 are connected with each other. The male connector 130 may be physically coupled to the female connector 14 of the main body 10. The male connector 130 serves to transmit an electric signal generated by the transducer module to the female connector 14 physically coupled thereto or to receive a control signal generated by the main body 10 from the female connector 14.

FIG. 1 illustrates a state in which the male connector 130 and the cable 120 are exposed to an outside. However, the male connector 130 and the cable 120 may be built in a housing forming the main body 10.

Meanwhile, a display 30 and the control panel 20 may be provided at the main body 10 of the medical apparatus 1. An input part 24 for allowing the user to control the medical apparatus 1 may be provided at the control panel 20. The input part 24 may receive not only setup information about the ultrasonic probe 100 but also various control commands from the user.

According to one embodiment, the setup information about the ultrasonic probe 100 includes gain information, zoom information, focus information, time gain compensation (TGC) information, depth information, frequency information, power information, frame average information, dynamic range information and so on. However, the setup information about the ultrasonic probe 100 is not limited to one embodiment and may include a variety of information set to take the ultrasonic image.

The information may be transmitted to the ultrasonic probe 100 through the cable 120, and the ultrasonic probe 100 may be set according to the received information. Furthermore, the main body 10 may receive various control commands like a transmitting command of the ultrasonic signal from the user through the input part 24 and then may transmit the control commands to the ultrasonic probe 100.

Meanwhile, the input part 24 may be realized in a keyboard, foot switch or foot pedal method. For example, the keyboard may be realized hardware-wise. Such a keyboard may include at least one of a switch, a key, a joystick and a trackball. As another example, the keyboard may be realized software-wise like a graphic user interface. In this case, the keyboard may be displayed through the display 30. The foot switch or the foot pedal may be provided at a lower portion of the main body 10, and the user may control an operation of the medical apparatus 1 using the foot pedal.

The display 30 may be realized in various well-known methods such as a cathode ray tube (CRT), a liquid crystal display (LCD), a light emitting diode (LED), a plasma display panel (PDP) and an organic light emitting diode (OLED) but is not limited thereto.

The display 30 may display the ultrasonic image of a target region in the object. The ultrasonic image displayed on the display 30 may be a two-dimensional ultrasonic image or a three-dimensional ultrasonic image, and various ultrasonic images may be displayed according to an operation mode of the medical apparatus 1. Also, the display 30 may display not only a menu or guide information required for an ultrasonic diagnosis but also information about an operation state of the ultrasonic probe 100.

According to one embodiment, the ultrasonic image includes an A-mode (amplitude mode) image, a B-mode (brightness mode) image and an M-mode (motion mode) image and also includes a C-mode (color mode) image and a D-mode (Doppler mode) image.

Hereinafter, the A-mode image is an ultrasonic image indicating an intensity of an ultrasonic signal corresponding to an echo ultrasonic signal, the B-mode image is an ultrasonic image indicating the intensity of the ultrasonic signal corresponding to the echo ultrasonic signal into brightness, and the M-mode image is an ultrasonic image indicating a movement of an object at a certain position according to a time. The D-mode image is an ultrasonic image indicating the moving object into a waveform using the Doppler effect, and the C-mode image is an ultrasonic image indicating the moving object in the form of a color spectrum.

Meanwhile, a subsidiary display 26 may be provided at the control panel 20. The subsidiary display 26 may provide relevant information like a menu or an auxiliary image for optimizing the ultrasonic image, or a graphic interface to the user.

Also, when the subsidiary display 26 is realized in a touchscreen type, the display 30 may also perform a function of the input part 24. That is, the main body 10 may receive various commands from the user through at least one of the display 30 and the input part 24. Further, although not shown in the drawings, a voice recognition sensor may be provided at the main body 10 and may receive a voice command from the user.

Hereinafter, a configuration of the ultrasonic probe will be more specifically described.

Figure 2:
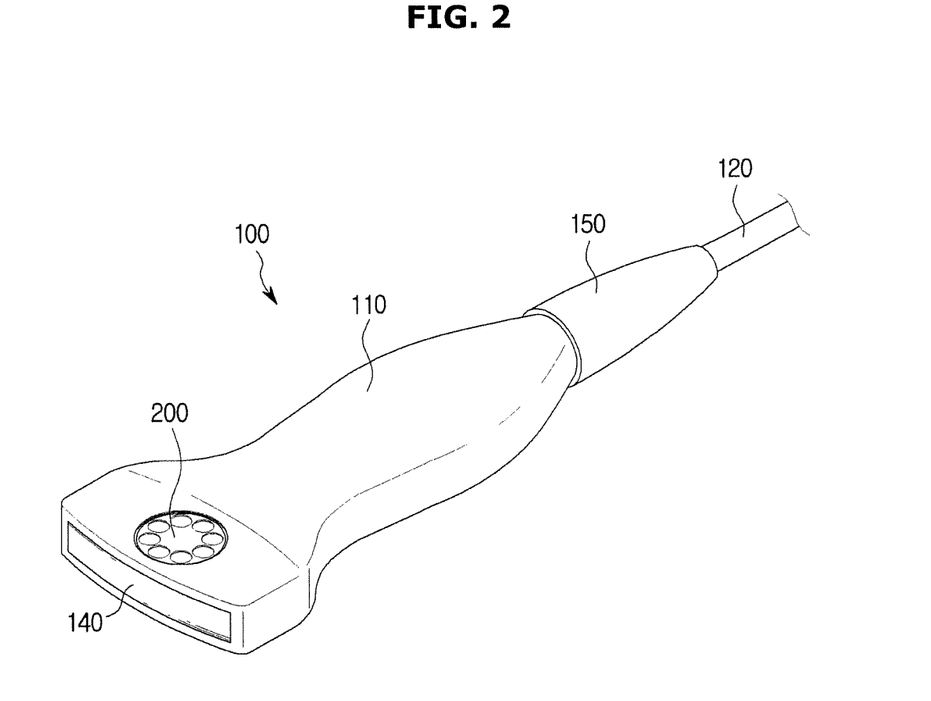
FIG. 2 is a perspective view of the ultrasonic probe according to one embodiment of the present disclosure.
Figure 3:
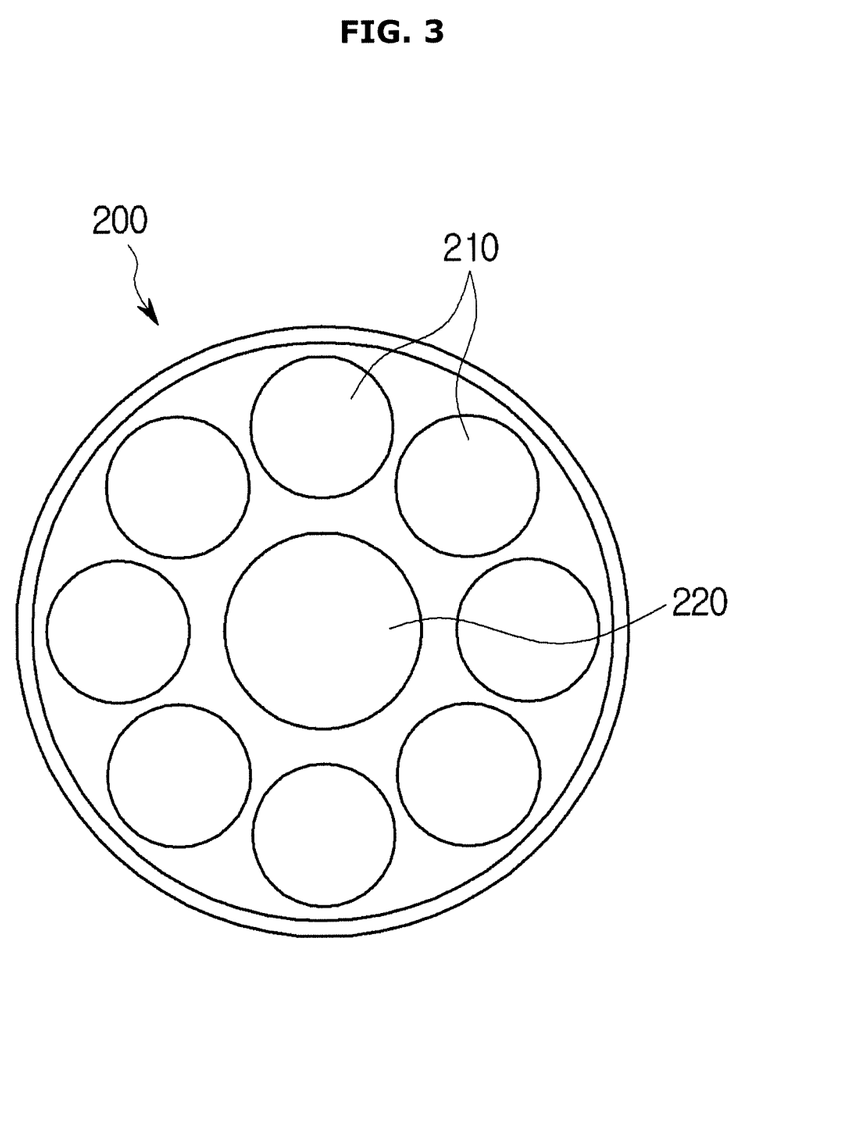
FIG. 3 is a view illustrating an indicator attached to the ultrasonic probe illustrated in FIG. 2.

FIG. 2 is a perspective view of the ultrasonic probe according to one embodiment of the present disclosure, and FIG. 3 is a view illustrating an indicator attached to the ultrasonic probe illustrated in FIG. 2.

Referring to FIG. 2, the ultrasonic probe 100 according to one embodiment of the present disclosure includes the case 110 in which the ultrasonic wave transmitting and receiving device, i.e., the transducer module is accommodated and the cable 120 for connecting the ultrasonic wave transmitting and receiving device with the main body 10 of the medical apparatus 1.

When an inspector uses the ultrasonic probe 100, the cable 120 may be sharply bent or twisted at an end of the case 110 of the ultrasonic probe 100. When the cable 120 is sharply bent or twisted, the cable 120 may be disconnected, or a jacket of the cable 120 may be damaged. In order to prevent the cable 120 from being sharply bent or twisted at the end of the case 110 of the ultrasonic probe 100, the ultrasonic probe 100 may include a strain relief 150 provided at the end of the case 110, to which the cable 120 is connected, to cover the cable 120. That is, the strain relief 150 is provided outside one end of the case 110 to prevent a damage of the cable 120.

The strain relief 150 may be formed of a soft material to allow the cable 120 to be gently curved. Although the strain relief 150 is formed of the soft material, the strain relief 150 should have a predetermined degree of hardness to prevent the cable 120 from being sharply bent. Therefore, the strain relief 150 may have a structure which is easily bent to one side while having the predetermined degree of hardness or a structure which may be bent in multi-stages.

A lens 140 is disposed at the other end of the case 110 to which the cable 120 is not connected. The transducer module disposed inside the case 110 may emit the generated ultrasonic wave to the object through the lens 140. Therefore, in the ultrasonic probe 100, the lens 140 is one of very important components. However, in the ultrasonic probe 100, since the lens 140 is exposed to the outside, it is easy to be damaged due to the user's carelessness.

The case in which the lens 140 of the ultrasonic probe 100 is damaged includes a case in which the user drops the lens 140 and thus the lens 140 is damaged or scratched, a case in which the lens 140 is neglected while being stained with an ultrasonic diagnosis gel and the ultrasonic diagnosis gel is dried thereon, a case in which the lens 140 is chemically deformed by an unauthorized disinfectant or cleaner, and so on. When the lens 140 of the ultrasonic probe 100 is damaged, a performance degradation of the ultrasonic probe 100, such as a degradation of resolution, may occur, or a problem such as discoloration and heating may be caused.

The ultrasonic probe 100 according to the present disclosure may include an indicator 200 for checking whether the lens 140 is chemically deformed by an unauthorized disinfectant or cleaner.

When the ultrasonic probe 100 is disinfected or cleaned with the unauthorized disinfectant or cleaner, the lens 140 may be deformed, a separation may occur at a bonded portion, or performance of the transducer module may be degraded due to an internal moisture intrusion. However, in various user environments, it is difficult for the user to previously recognize a chemical composition of various disinfectants and cleaners and to determine whether it is usable, and it is also difficult to obtain information about whether it is usable.

The indicator 200 according to the present disclosure may be attached to one outer surface of the case 110 and may include a reacting part 210 reacting with a certain chemical component. The reacting part 210 may be disposed adjacent to the lens 140.

The reacting part 210 of the indicator 200 may be provided to indicate whether it reacts by a change in a color thereof. That is, the reacting part 210 of the indicator 200 may include a material of which the color is changed by reacting with an unauthorized certain chemical component. Also, the reacting part 210 of the indicator 200 may include a material of which the color is changed in stages or changed into another color according to a concentration of an unauthorized certain chemical material included in the disinfectant, or may include a material of which the color is changed in stages or changed into another color according to a pH concentration of the unauthorized certain chemical material included in the disinfectant.

Also, the reacting part 210 of the indicator 200 may be provided to indicate whether it reacts by disappearance of the reacting part 210. That is, the reacting part 210 may include a material disappeared by reacting with the unauthorized certain chemical component. The reacting part 210 including the material to be disappeared may be configured so that the material to be disappeared is coated on a background having a color different from that of the material to be disappeared and the color of the background is exposed when the material is disappeared.

For example, an iodine component of povidone as an unauthorized disinfectant is discolored into purple when reacting with starch as a glucose polymer, and a peroxide reacts with catalase, zinc thiophophate and mercaptan, and an ethylene oxide used in the cleaner reacts with ether. Also, a kind of acid causing the separation of a layered part in the transducer module reacts with thymol blue, methyl orange, bromothymol blue, phenolphthalein or the like according to a pH concentration thereof and is then discolored.

The indicator 200 may include a plurality of reacting parts 210 to detect a plurality of unauthorized chemical components. Each of the plurality of reacting parts 210 may be provided to react with each of chemical components different from each other. Meanwhile, each of the plurality of reacting parts 210 may be provided to react according to a concentration of a certain chemical component.

The indicator 200 may include an information provider 220 providing information for checking whether each of the reacting parts 210 reacts. That is, the information provider 220 may provide information for determining or checking whether each of the reacting parts 210 reacts with the certain chemical component. The information provider 220 may be configured to provide information of a name or a concentration of the certain chemical component with which each of the reacting parts 210 reacts.

In particular, when the indicator 200 includes the plurality of reacting parts 210, the information provider 220 may be configured to provide information of a chemical component with which the reacting part 210 among the plurality of reacting parts 210 in which a reactant is discolored or disappeared reacts and the name or the concentration of the reacting chemical component.

The indicator 200 may be replaceably attached to the case 110 so that the reacting part 210 is replaced after an reaction with the certain chemical component. Meanwhile, when the indicator 200 includes the plurality of reacting parts 210, the indicator 200 may be configured so that only the reacting part 210 reacted with the certain chemical component is replaced.

Figure 4:
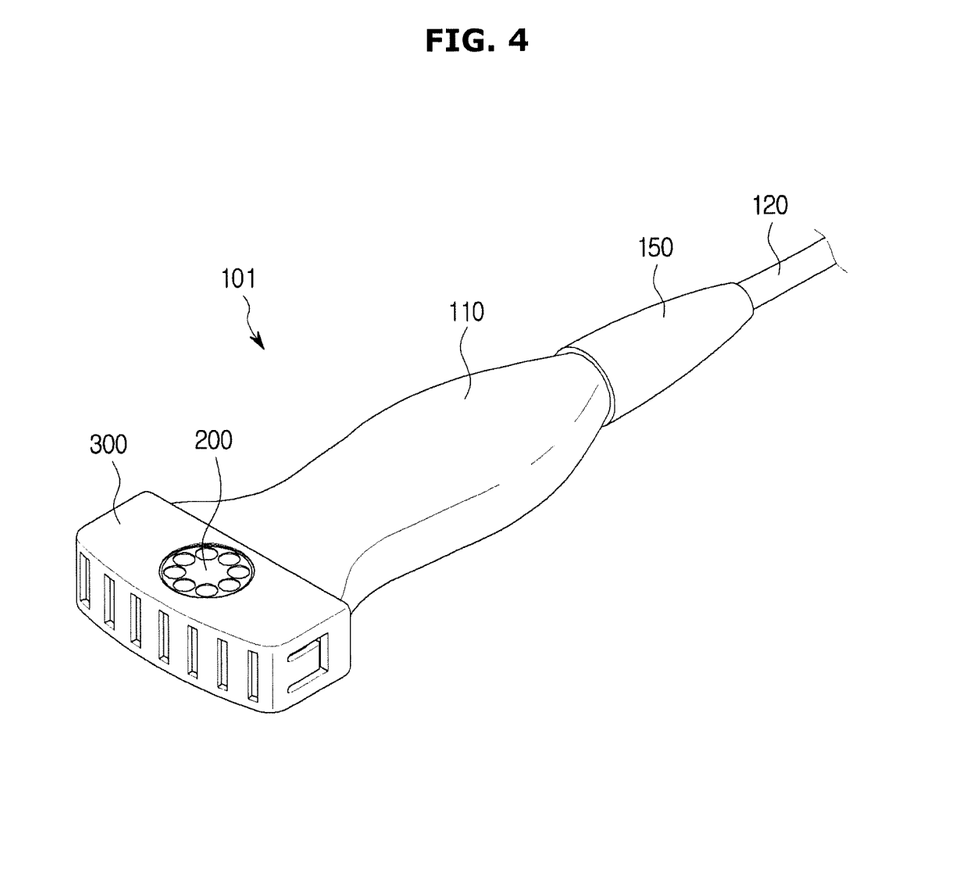
FIG. 4 is a perspective view of an ultrasonic probe according to another embodiment of the present disclosure.
Figure 5:
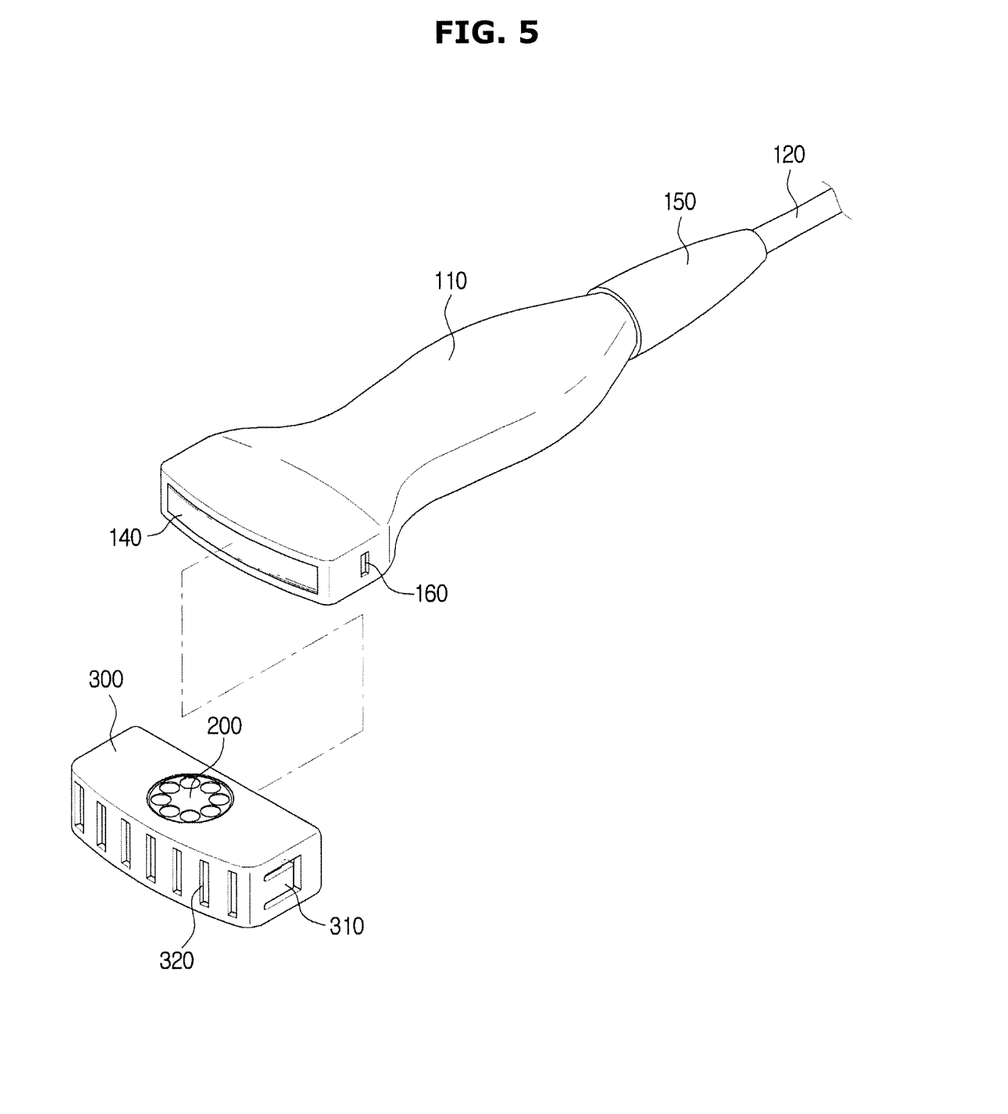
FIG. 5 is a perspective view illustrating a state in which a cap is separated from the ultrasonic probe illustrated in FIG. 4.
Figure 6:
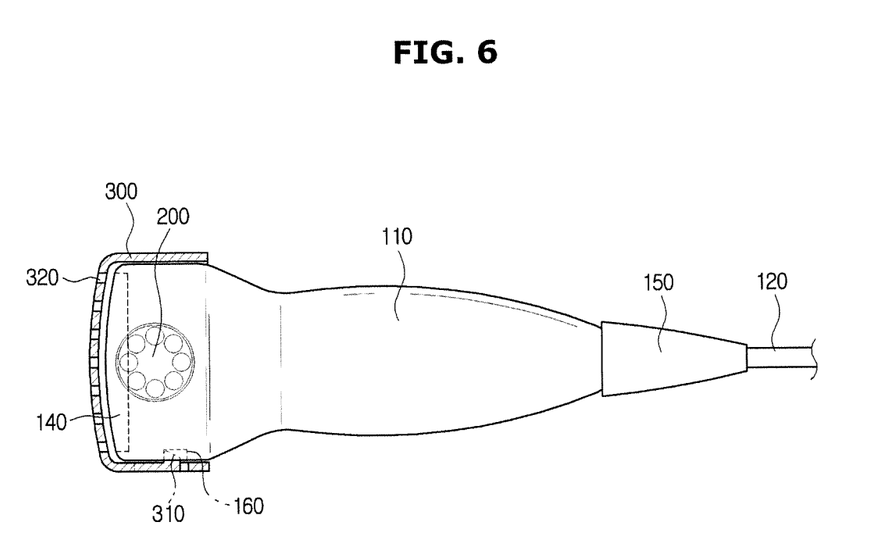
FIG. 6 is a view schematically illustrating a cross section of the ultrasonic probe illustrated in FIG. 4.

FIG. 4 is a perspective view of an ultrasonic probe according to another embodiment of the present disclosure, FIG. 5 is a perspective view illustrating a state in which a cap is separated from the ultrasonic probe illustrated in FIG. 4, and FIG. 6 is a view schematically illustrating a cross section of the ultrasonic probe illustrated in FIG. 4.

Referring to FIGS. 4 to 6, an ultrasonic probe 101 may include a case 110, a cable 120, a lens 140 and a strain relief 150. Since the case 110, the cable 120, the lens 140 and the strain relief 150 are the same as those described above and illustrated in FIG. 2, detailed descriptions thereof will be omitted.

The ultrasonic probe 101 may include a configuration for allowing the inspector to check left and right directions of the lens 140. Specifically, the case 110 may include a groove 160 for checking the left and right directions of the lens 140. The groove 160 may be provided at one side surface of the case 110 and may be disposed adjacent to the lens 140.

Since the groove 160 is formed at only one side surface of the case 110, the inspector may check a position of the groove 160 when gripping the ultrasonic probe 101 and may confirm the left and right directions of the lens 140.

When the ultrasonic probe 101 is dropped on a floor or collides with equipment therearound due to the user's carelessness, the lens 140 of the ultrasonic probe 101 may be damaged. Also, the lens 140 may be scratched by a sharp tool.

The ultrasonic probe 101 according to the present disclosure may include a cap 300 separably coupled with the case 110 to protect the lens 140. The user may take off the cap 300 when using the ultrasonic probe 101 and may couple the cap 300 to the case 110 when storing the ultrasonic probe 101.

The cap 300 may be coupled to an end of the case 110, at which the lens 140 is disposed, to protect the lens 140 of the ultrasonic probe 101. The cap 300 may be formed to have a shape similar to that of the end of the case 110 at which the lens 140 is disposed.

When an inner side surface of the cap 300 comes in contact with the lens 140 while the cap 300 is coupled to the case 110, the lens 140 may be damaged. Therefore, the cap 300 may be formed to be spaced apart from the lens 140 at a predetermined distance when being coupled to the case 110.

The cap 300 may include a hook 310 allowed to be coupled to the groove 160 provided at the case 110 to confirm the left and right directions of the lens 140. When the cap 300 is coupled to the case 110, the hook 310 may be coupled to the groove 160 provided at the case 110, and thus the cap 300 may be prevented from being undesirably separated from the case 110.

Although not illustrated in the drawings, the configuration for checking the left and right directions of the lens 140 may be formed into a protrusion. The protrusion may be provided at one side surface of the case 110 and may be disposed adjacent to the lens 140.

When the configuration for checking the left and right directions of the lens 140 is formed into the protrusion, the cap 300 may include a groove for accommodating the protrusion provided at the case 110 and thus may be coupled to the case 110.

To allow the ultrasonic probe 101 to be cleaned or disinfected while the cap 300 is coupled to the case 110, the cap 300 may include a hole 320 provided to allow a disinfectant or a cleaner to pass therethrough. Although not illustrated in the drawings, one surface of the cap 300, preferably, that corresponding to the lens 140 may be formed into a mesh to allow the disinfectant or the cleaner to pass therethrough.

An indicator 200 may be attached to one outer surface of the cap 300. Since the indicator 200 is the same as that described above and illustrated in FIG. 3, detailed description thereof will be omitted.

Although not illustrated in the drawings, the indicator 200 may be attached to one outer surface of the case 110. Specifically, the cap 300 may be formed as a transparent member, and the indicator 200 may be attached to an outer surface of the case 110 to be adjacent to the lens 140. The indicator 200 according to the present disclosure may be attached to not only the case 110 of the ultrasonic probe 101 or the cap 300 but also the main body 10 of the medical apparatus 1, the control panel 20 and so on, to which the disinfectant or the cleaner may be applied, to detect an unusable disinfectant or cleaner.

The ultrasonic probe according to the spirit of the present disclosure can check whether the disinfectant or the cleaner is usable and thus can prevent the ultrasonic probe from being chemically deformed or damaged.

The above-mentioned detailed description exemplifies the inventive concept. Furthermore, the above-mentioned contents describe the exemplary embodiment of the inventive concept, and the inventive concept may be used in various other combinations, changes, and environments. That is, the inventive concept can be modified and corrected without departing from the scope of the inventive concept that is disclosed in the specification, the equivalent scope to the written disclosures, and/or the technical or knowledge range of those skilled in the art. The written embodiment describes the best state for implementing the technical spirit of the inventive concept, and various changes required in the detailed application fields and purposes of the inventive concept can be made. Accordingly, the detailed description of the inventive concept is not intended to restrict the inventive concept in the disclosed embodiment state. Furthermore, it should be construed that the attached claims include other embodiments.

What is claimed is:

1. An ultrasonic probe comprising:
   a case in which an ultrasonic wave transmitting and receiving device is accommodated;
   a lens provided at one end of the case; and
   an indicator attached to an outer surface of the case,
   wherein the indicator comprises:
      a reacting part configured to react with a certain chemical component deforming or damaging the lens, and
      an information provider separate from the reacting part and providing information for checking whether the reacting part reacts, and
   wherein the indicator is spaced apart from the lens to prevent the lens from being in contact with the chemical component deforming or damaging the lens.

2. The ultrasonic probe according to claim 1, wherein the indicator is disposed adjacent to the lens.

3. The ultrasonic probe according to claim 1, wherein the indicator includes a plurality of reacting parts, and the plurality of reacting parts react with chemical components deforming or damaging the lens different from each other, respectively.

4. The ultrasonic probe according to claim 1, wherein the reacting part includes a material of which a color is changed when reacting with the chemical component.

5. The ultrasonic probe according to claim 4, wherein the reacting part includes a material of which the color is changed in stages according to a concentration of the chemical material or changed into different color according to the concentration of the chemical material.

6. The ultrasonic probe according to claim 1, wherein the reacting part includes a material disappeared by reacting with the chemical component.

7. The ultrasonic probe according to claim 6, wherein the reacting part is configured so that a background of a color different from that of the material is exposed when the material is disappeared.

8. The ultrasonic probe according to claim 1, wherein the indicator is replaceably attached to the case.

9. The ultrasonic probe according to claim 1, wherein the information provider is configured to provide information of a name or a concentration of the chemical component with which the reacting part reacts.

10. The ultrasonic probe according to claim 1, wherein the indicator includes a plurality of reacting parts, and each of the plurality of reacting parts reacts according to a concentration of the chemical component.

11. An ultrasonic probe comprising:
    a case in which an ultrasonic wave transmitting and receiving device is accommodated;
    a lens provided at one end of the case;
    a cap separably coupled to the case to protect the lens; and
    an indicator disposed apart from the lens and configured to prevent the lens from being chemically deformed or damaged,
    wherein the indicator comprises:
       a reacting part configured to react with a certain chemical component deforming or damaging the lens, and
       an information provider separate from the reacting part and providing information for checking whether the reacting part reacts.

12. The ultrasonic probe according to claim 11, wherein the cap includes a hole or a mesh provided to allow a disinfectant or a cleaner to pass therethrough.

13. The ultrasonic probe according to claim 11, wherein the indicator is attached to an outer surface of the cap.

14. The ultrasonic probe according to claim 11, wherein the indicator is attached to an outer surface of the case adjacent to the lens.

15. The ultrasonic probe according to claim 11, wherein the case includes a groove for checking left and right directions of the lens, and the cap includes a hook coupled to the groove.

16. The ultrasonic probe according to claim 11, wherein the cap is configured to be spaced apart from the lens at a predetermined distance when being coupled with the case.

* * * * *